(12) United States Patent
Schmidt

(10) Patent No.: US 6,809,324 B1
(45) Date of Patent: Oct. 26, 2004

(54) SCANNING DEVICE, ESPECIALLY FOR DETECTING FLUORESCENT LIGHT

(75) Inventor: Stefan Schmidt, Kiel (DE)

(73) Assignee: Carl Zeiss Jena GmbH, Jena (DE)

(*) Notice: Subject to any disclaimer, the term of this patent is extended or adjusted under 35 U.S.C. 154(b) by 0 days.

(21) Appl. No.: 09/979,382

(22) PCT Filed: May 18, 2000

(86) PCT No.: PCT/EP00/04492
§ 371 (c)(1),
(2), (4) Date: Nov. 19, 2001

(87) PCT Pub. No.: WO00/72077
PCT Pub. Date: Nov. 30, 2000

(30) Foreign Application Priority Data

May 19, 1999 (DE) ......................................... 199 23 822

(51) Int. Cl.⁷ .............................................. G01N 21/64
(52) U.S. Cl. ................................. 250/459.1; 250/458.1
(58) Field of Search ......................... 250/458.1, 459.1, 250/461.1, 461.2

(56) References Cited

U.S. PATENT DOCUMENTS 5,315,375 A   5/1994  Allen
5,381,224 A * 1/1995  Dixon et al. .................. 356/72
5,796,112 A   8/1998  Ichie

FOREIGN PATENT DOCUMENTS

| DE | 31 49 728   | 7/1982  |
| DE | 37 42 806   | 7/1989  |
| DE | 692 13 789  | 9/1992  |
| DE | 41 11 903   | 10/1992 |
| DE | 43 30 347   | 3/1995  |
| DE | 43 41 462   | 6/1995  |
| DE | 43 43 076   | 6/1995  |
| DE | 44 45 214   | 6/1996  |
| DE | 196 30 322  | 1/1997  |
| WO | WO 96/18205 | 6/1996  |

* cited by examiner

Primary Examiner—Constantine Hannaher
Assistant Examiner—Timothy Moran
(74) Attorney, Agent, or Firm—Reed Smith LLP

(57) ABSTRACT

Optical arrangement for the suppression of stray light originating from an illuminated specimen detected via an objective, with blocking out or reflecting out in part of the beam path in order to generate a shadow area for stray light in the image plane.

8 Claims, 6 Drawing Sheets

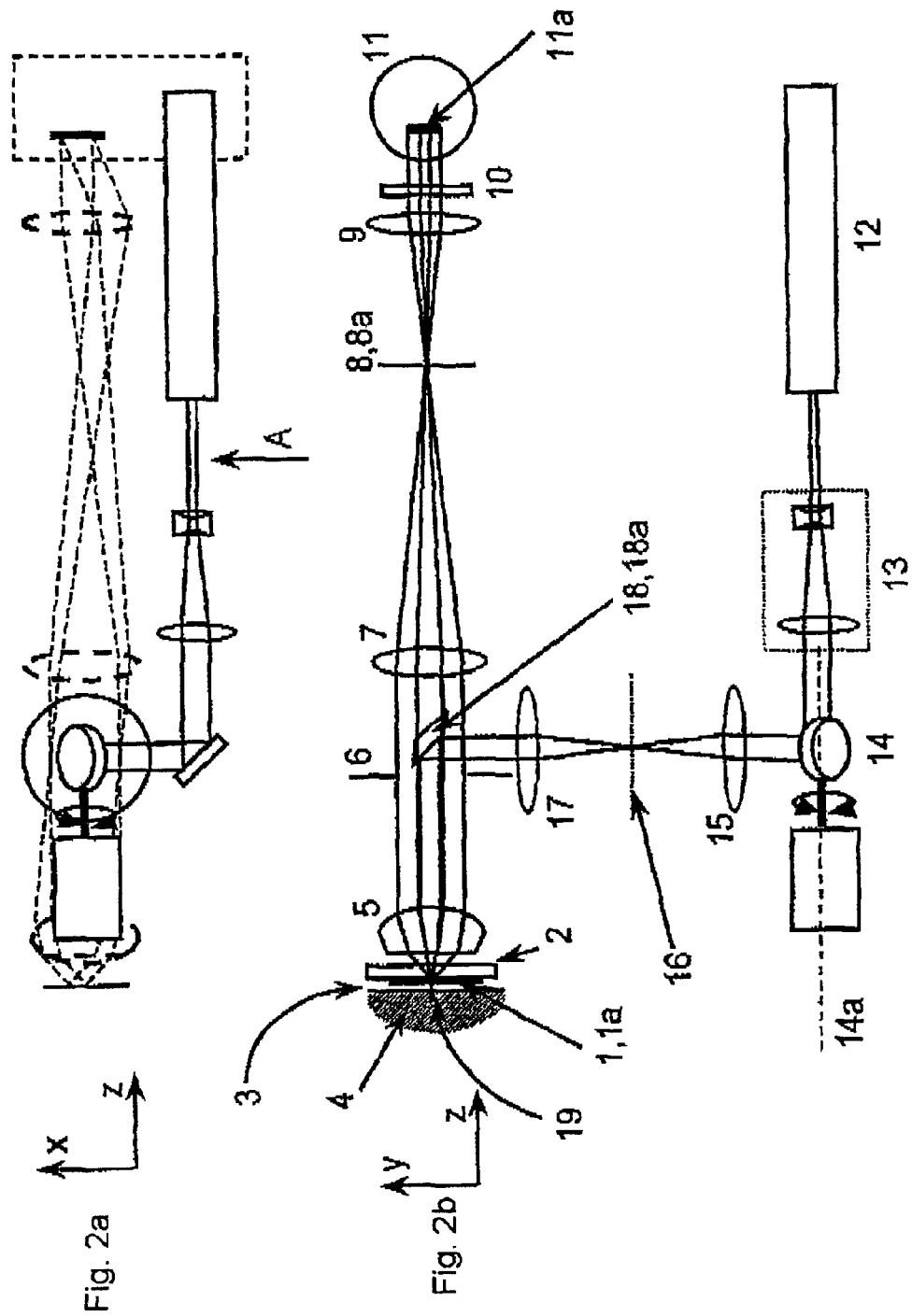
Figure 2  Beam path for a line in x-direction

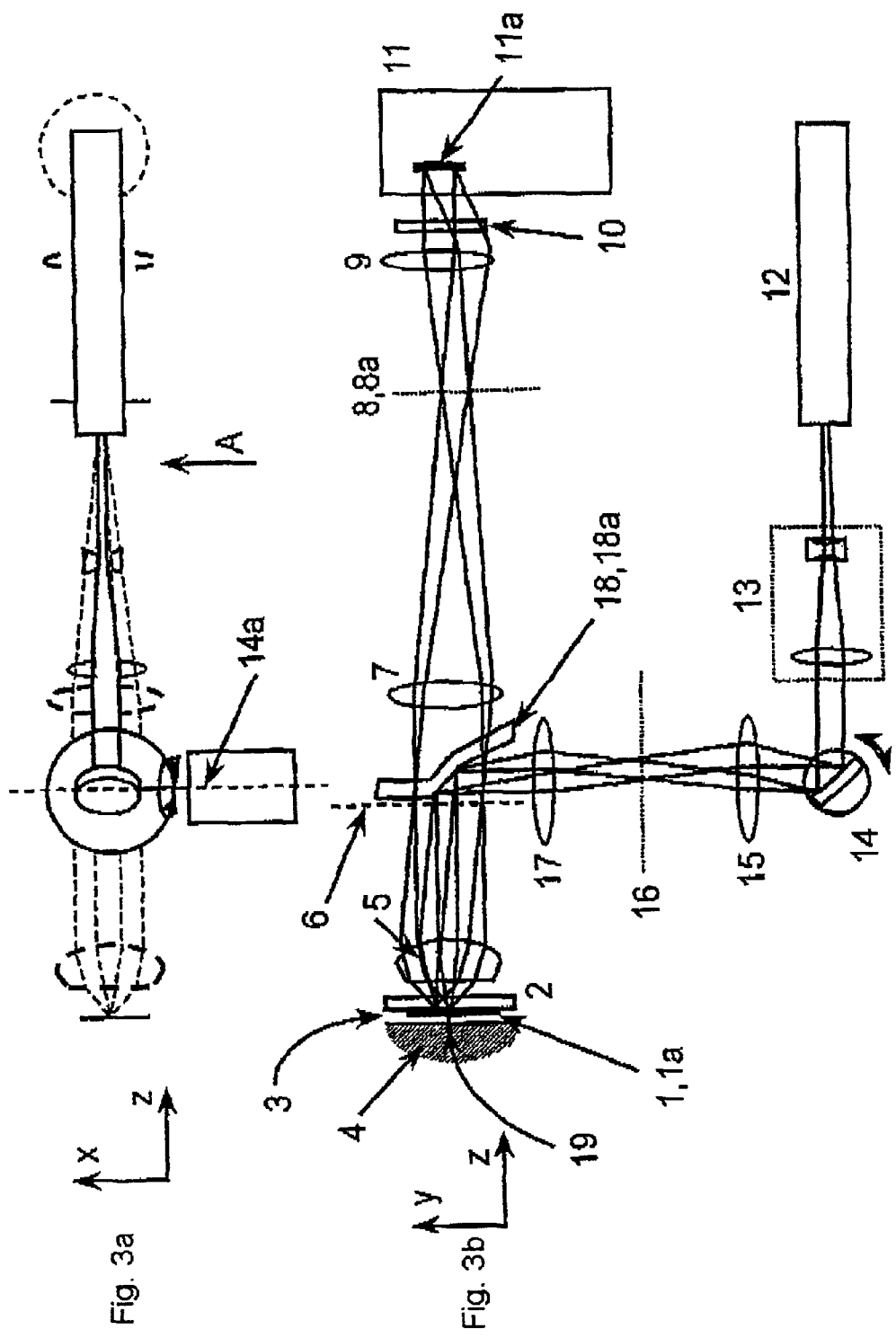

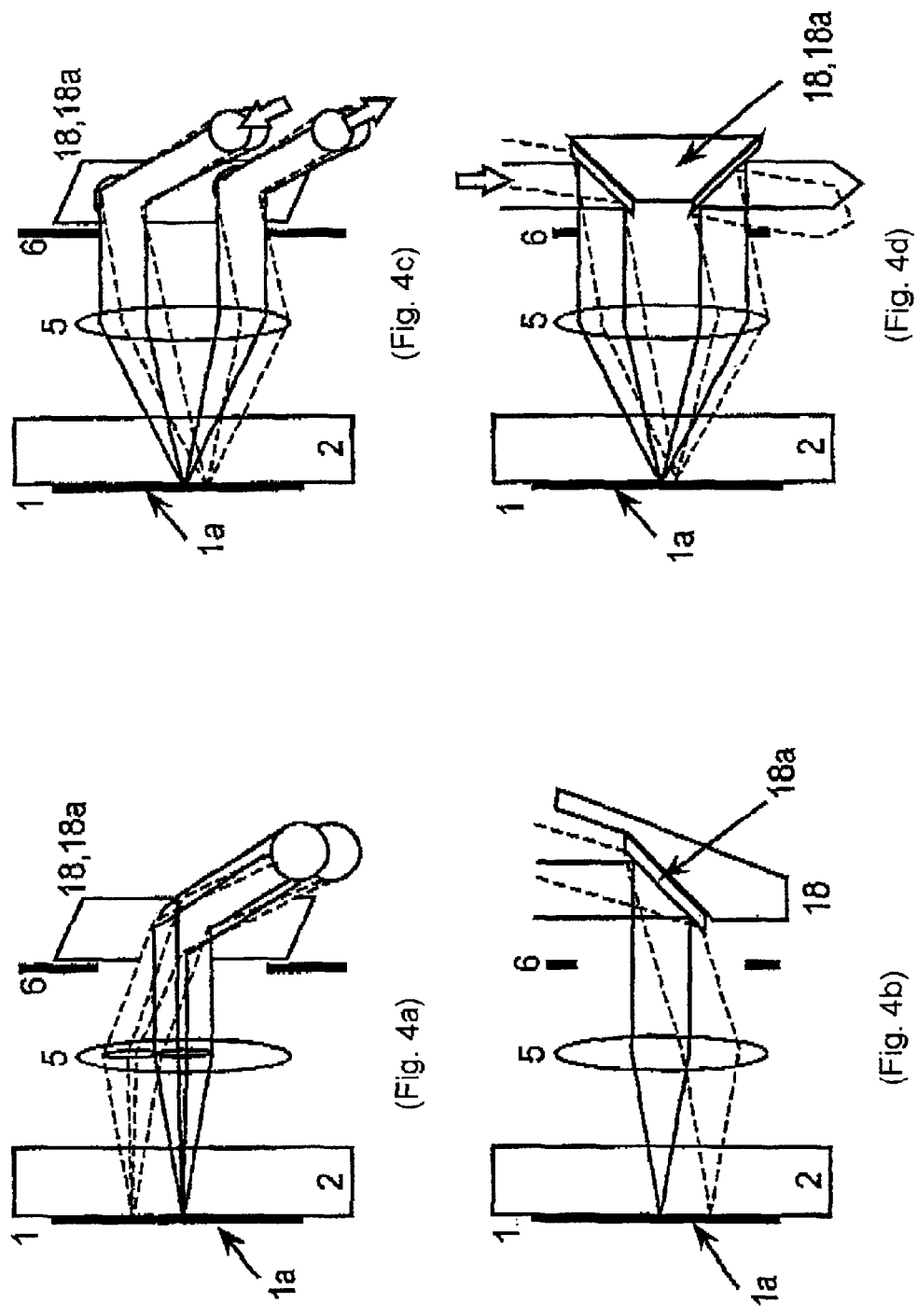
Figure 4    Possible implementations of in-reflection

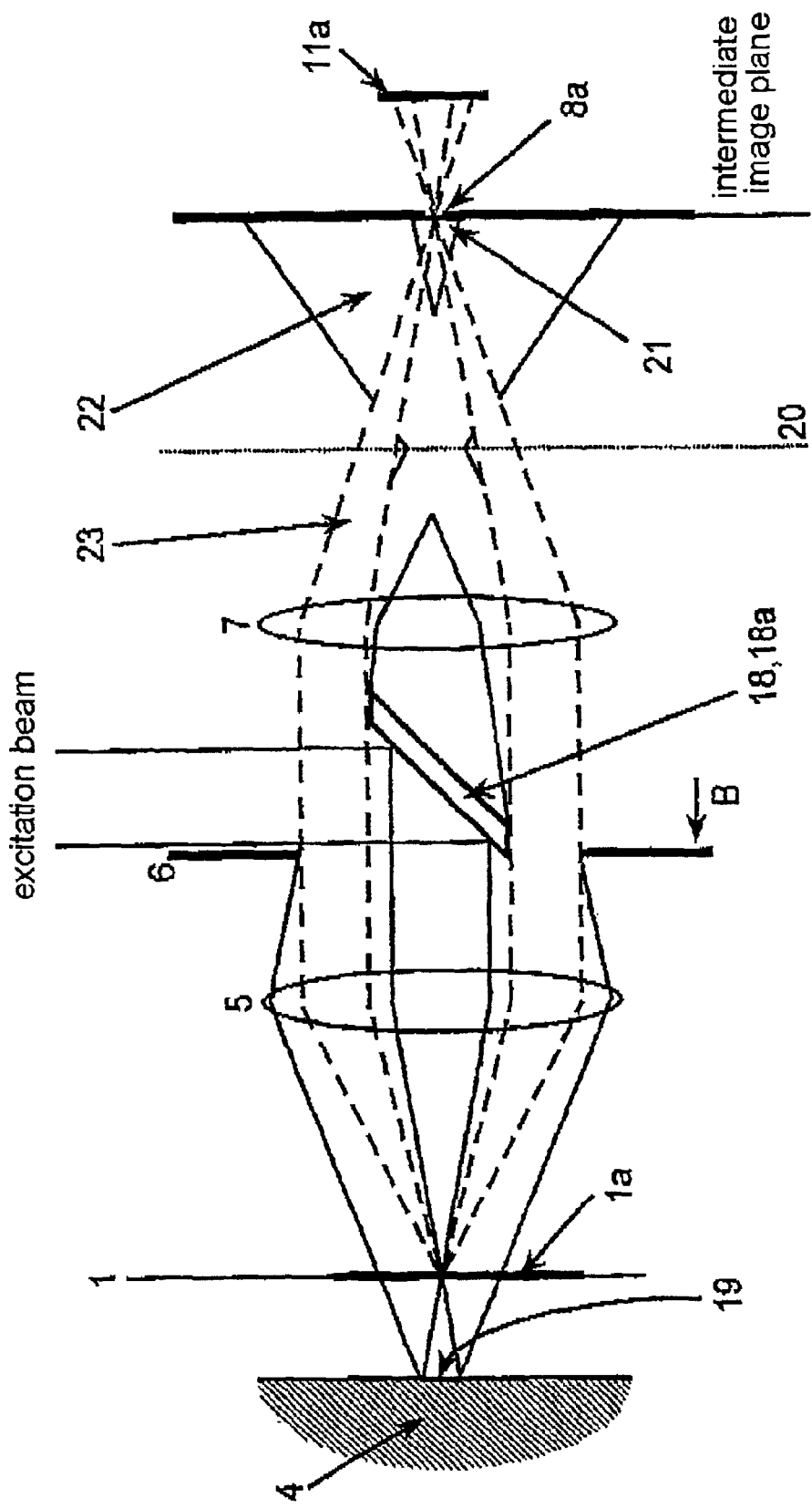
Figure 5    Principle of operation of blocking out

Figure 6   Constructions of pupil (cross section)
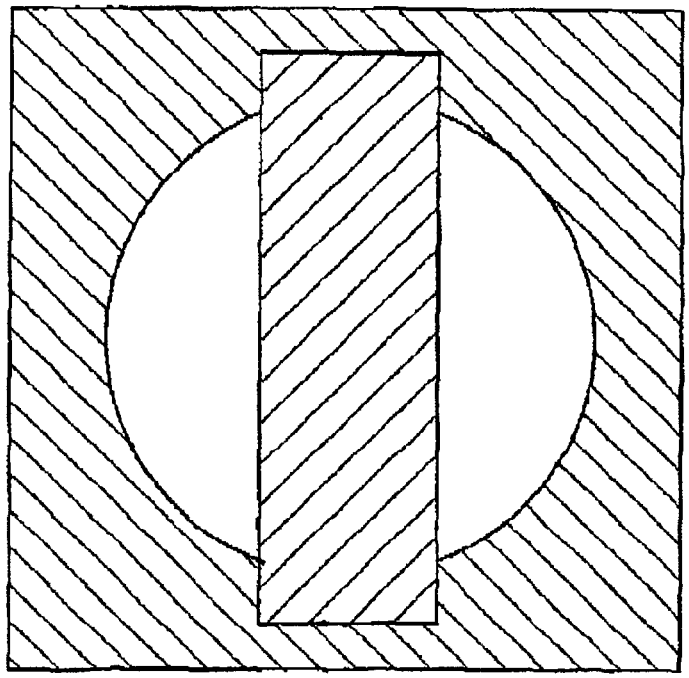
(Fig. 6b)
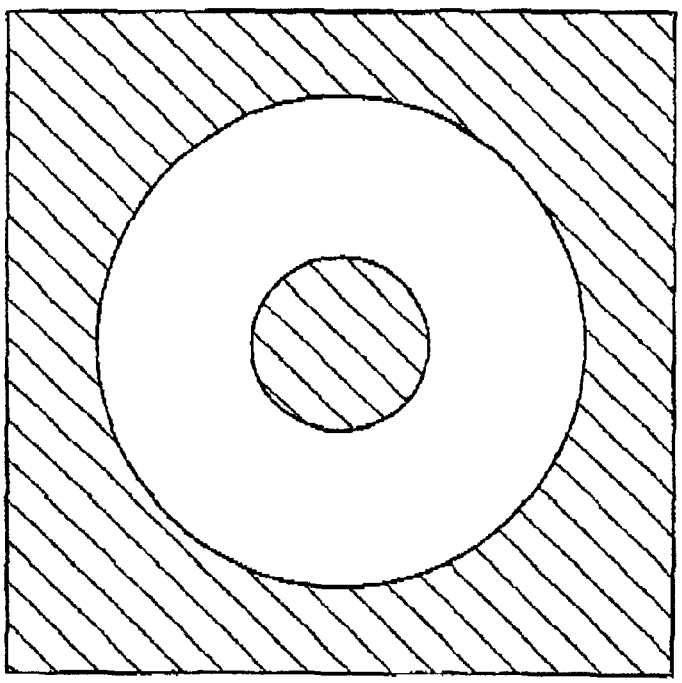
(Fig. 6a)

SCANNING DEVICE, ESPECIALLY FOR DETECTING FLUORESCENT LIGHT

CROSS-REFERENCE TO RELATED APPLICATIONS

This application claims priority of PCT application Ser. No. PCT/EP00/04492, filed May 18, 2000 and German Application No. DE 199 23 822.7, filed May 19, 1999, the complete disclosures of which are hereby incorporated by reference.

FIELD OF THE INVENTION

The invention is directed to the detection and measurement of fluorescence of a thin layer of several 100-nm thickness of dye-labeled molecules on a glass substrate. With reference to FIG. 1, the thin layer is shown as element 1a and the glass substrate as element 2.

OBJECT OF THE INVENTION

The primary object of the invention is to detect the fluorescence efficiency quantitatively depending on the lateral location in the layer (1a).

As shown in FIG. 1, in order for the thin, optically active layer (1a) to be subject to chemical process prior to or during optical observation, it lies on the inside of a channel (3) which is filled with liquid, for example, an aqueous solution. A process of this kind is, for example, staining the layer (1a) with a dye solution.

The channel (3) is formed by the substrate and a channel back wall (4) which is shown in section. The channel back wall (4) can be made of different materials. Plastic which is excited to fluorescence during illumination is often used. In this case, the emission of the channel back wall interferes with optical observation.

The back reflection and backscattering of excitation light in the objective (5) is also troublesome. Back reflection and backscattering take place not only at the channel back wall but also on the upper side and underside of the substrate.

SUMMARY OF THE INVENTION

In the instrument described herein in accordance with the invention, observation and excitation are carried out with an objective (5) through the glass substrate (2). The optical design of the instrument is carried out in such a way that observation is not falsified by interfering light. In particular, the optical construction of the instrument prevents the fluorescent light of the channel back wall (4) or scattered light and back-reflected excitation light from impinging on the detector surface (11a) of the instrument.

BRIEF DESCRIPTION OF THE DRAWINGS

In the drawings:

FIGS. 2a and 2b illustrate in schematic representation the beam path in accordance with the invention in the X-direction; FIG. 2b is shown viewing FIG. 2a along line A shown in FIG. 2a;

FIGS. 3a and 3b illustrate in schematic representation the beam path in accordance with the invention in the Y-direction; FIG. 3b is shown viewing FIG. 3a along line A shown in FIG. 3a;

FIGS. 4a–4d show possible arrangements in schematic form of the opaque diaphragm and of the mirror held by the diaphragm;

FIG. 5 shows in schematic representation the principle of operation of the blocking out aspect of the invention; and FIGS. 6a and 6b show construction of the pupil in cross-section in accordance with the invention.

DESCRIPTION OF THE PREFERRED EMBODIMENTS

Figure 1:
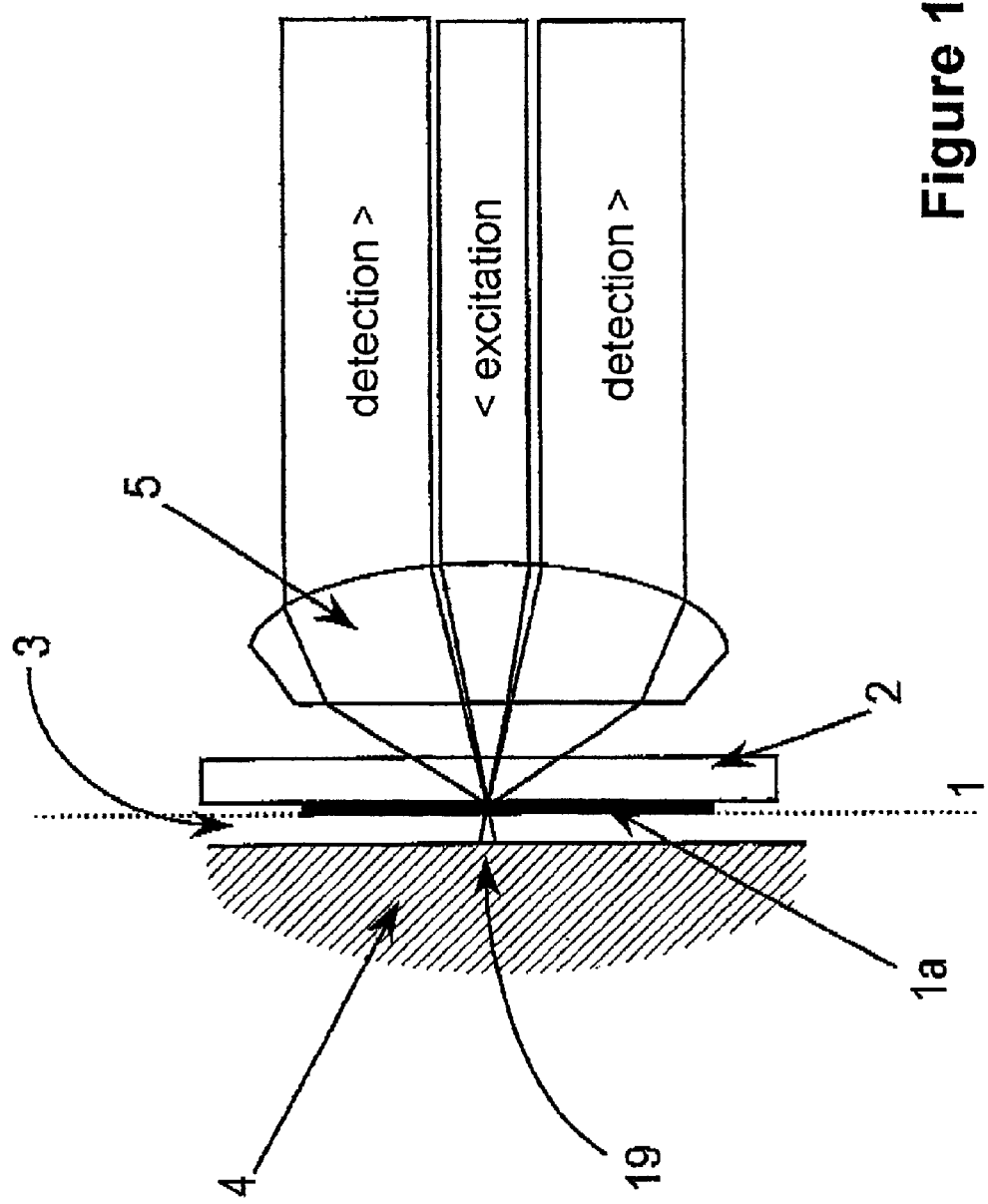
FIG. 1 is a schematic representation of an arrangement in accordance with the invention showing specimen geometry.

With reference to FIGS. 1 and FIG. 3:

An objective (5) is used to focus the collimated excitation light on the specimen (active layer (1a)). The objective (5) also serves to collect the light emitted by the specimen. A diaphragm arrangement (18) is arranged in the vicinity of the pupil plane (6). The diaphragm arrangement (18) includes a mirror for in reflection of the excitation light. The projective lens (7), together with the objective lens (5), images the object plane in the detection-side intermediate image plane (8).

Detector optics (9) are used for homogeneous illumination of the detector (11) and expansion optics (13) are used for expanding the laser beam.

The scanning objective (15) transforms the deflection of the laser beam into a linear movement of the excitation spot. Together with the objective (5), the tube optics (17) in the excitation channel images the excitation-side intermediate image plane (16) in the object plane (1).

An autofocus unit enables automatic adjustment of the thin specimen layer (1a) in the object plane (1).

Excitation Beam Path:
(FIG. 2 and FIG. 3)

FIGS. 2b, 3b are views of FIGS. 2a, 3a considered in the direction of arrow A.

A laser (12) serves as light source. The cross section of the collimated laser beam is increased by expansion optics (13). The expanded beam impinges on the scanning mirror (14) arranged in the pupil of the scanning objective (15). The scanning objective (15) focuses the light deflected by the scanning mirror (14) in the excitation-side intermediate image plane (16). From the intermediate image plane (16), the light is received and collimated by the tube optics (17). The light is deflected by a mirror (18a) into the objective (5) and focused by the latter in the object plane (1). In this way, a small excitation spot is formed in the object plane (1) and can be moved back and forth on a line by means of the scanning mirror (14).

The illuminated aperture must be large enough (NA= 0.17) to generate a sufficiently small diameter (5 $\mu$m) of focus for the desired lateral resolution. Accordingly, the beam cross section of the laser must be increased sufficiently by the expansion optics (13).

In order to move the excitation spot in the object plane (1) on a straight line, the scanning mirror (14) is tilted about the axis (14a, parallel to direction in FIG. 2; parallel to x-direction in FIG. 3) extending at right angles to the plane of the incident and reflected beam. The entire specimen surface can be scanned together with a linear movement of the specimen at right angles to the movement of the excitation spot (line).

The scanning objective (15) and the tube optics must be adapted to one another in such a way that the illumination beam always enters completely through the pupil (6) of the objective and always impinges completely on the mirror (18a). The objective (5), tube optics (17) and scanning objective (15) together satisfy the F-theta condition; that is, the relationship between the angle of the scanning mirror (14) and the location of the focus in the object plane is linear.

The excitation light is reflected into the objective (5) by a mirror (18a) which is fastened to the diaphragm arrangement (18).

Only part of the aperture of the objective (5) is blocked out by the surface of the mirror (18a) and diaphragm arrangement (18), so that the light emitted by the specimen can go past the mirror (18a) and diaphragm arrangement (18) into the projective (7) (see FIG. 6) and, accordingly, reach the detector.

The excitation beam is reflected at the surface of the substrate (2) and at the interface between the substrate (2) and the liquid in the channel (3). The incident angle of the excitation beam is selected in such a way that the reflected bundles are kept away from the detection beam path by the strip-shaped diaphragm arrangement (18) or the mirror itself.

FIG. 4:

Possible arrangements of the opaque strip-shaped diaphragm (18) and of the mirror held by the latter are shown in FIGS. 4a–4d. FIG. 4a shows an arrangement for vertical telecentric incidence of the excitation beam on the specimen, wherein the scanned line lies in the same direction as the excitation beam (y-direction) before being reflected in. Similar to FIG. 3 (18, 18a), FIG. 4b shows an arrangement for vertical incidence of the excitation beam on the specimen, wherein the scanned line lies at right angles (x-direction) to that of the excitation beam before being reflected in. FIGS. 4c and 4d show arrangements with oblique incidence of the excitation beam on the specimen with decoupling of incident and reflected beam, wherein the angle of incidence is selected in such a way that the reflected beams are stopped by the strip-shaped diaphragm and can be reflected out of the detection beam path. It is also possible for all diaphragms shown herein to be constructed as mirrors.

The excitation light reflected back from the substrate surface or from the interface between substrate and liquid can be directed to a detector after being reflected out of the detection beam path. The output can then be measured for purposes of reference or calibration.

Detection Beam Path:

(FIG. 2 and FIG. 3)

The object plane (1) is imaged in the detection-side intermediate image plane (8) through the objective (5) and the projective (7) in the detection beam path. A slit diaphragm (8a) in the intermediate image plane (8) serves to suppress stray light. Optics (9) in front of the detector (11) provide for homogeneous illumination of the detector surface (11a).

A bandpass filter (10) which defines the spectral range to be detected is located directly in front of the detector.

The fluorescent light proceeding from the active layer (1a) is collected and collimated by the objective (5). A strip is blocked out of the collimated bundle in the pupil plane (6) of the objective. The strip lies parallel to the line on which the excitation spot moves and extends through the center of the pupil (6).

The blocking out of the strip and the in-reflection of the excitation light need not necessarily be located in the pupil of the objective in an optical arrangement for scanning a line. A movement of the beam bundle parallel to the direction of the blocked out strip in the plane in which in-reflection is carried out is permissible and does not impair the effect of the blocking out.

There is clear passage through the pupil (6) on both sides of the strip, so that a sufficiently large solid angle is available for detection of fluorescent light.

The blocking out of a strip has two functions:

a) In-reflection (18) of the excitation light is located in the blocking out area.

b) Fluorescent light in the spectral range to be detected occurs at the side of the channel (channel back wall (4)) located opposite the substrate (2) with the active layer (1a) due to the illumination by the excitation beam. This light is not suppressed by the bandpass filter (10) in front of the detector (11). Since the source of this light is expanded because of the defocused excitation and since it does not lie in the object plane (1), the greater part of this emission is stopped by the slit diaphragm (8a) in the intermediate image plane (8). In addition, a shadow area located above the slit (8a) in the intermediate image plane (8) is formed for this light by the blocked out strips. Fluorescent light from the channel back wall (4) can now only reach the detector surface (11a) indirectly via the scattering at the components of the beam path.

FIGS. 5 and 6: Principle of operation of blocking out:

FIGS. 5 and 6 illustrate the principle of operation and show possible constructions of the diaphragm.

The in-reflection and blocking out correspond in analogous manner to the variants shown in FIGS. 4a and 4b. The viewing direction in FIG. 6 corresponds to a view in direction of arrow B in FIG. 5.

By means of blocking out, a shadow area is formed in the image plane conjugate to the object plane for light whose source is spatially limited and does not lie in the object plane. The defocused excitation spot (19) on the channel back wall (4) or substrate surface is such a source for stray light.

Ideally, the blocking means (18) are large enough so that a core shadow area (21) is formed in the image plane (8) for the stray light and the diaphragm aperture (8a) confocal to the excitation focus lies completely within this core shadow area (21). Stray light (22) from the area of the defocused excitation spot in planes that are sufficiently far away from the object plane can then reach the detector surface (11a) only indirectly by scattering at the components of the beam path. In contrast, the useful light (23) from the area of the focused excitation beam in the object plane (1) passes the confocal diaphragm aperture (8a) unimpeded and reaches the detector surface (11a).

In order to achieve good blocking out of stray light (22), the core shadow area (21) must be sufficiently large so as to be greater than the aperture of the confocal diaphragm in every case.

In the case of a pinhole, this means that the blocked out aperture must be greater than the aperture of the excitation beam path.

When the confocal diaphragm is constructed as a slit, the blocked out aperture in the plane vertical to the slit must be greater than the aperture of the excitation beam path. The whole aperture must be covered in the plane parallel to the slit.

With a slit width corresponding to ten-times the diffraction-limited spot in the image plane, the blocked out sagittal aperture must be 5 to 10% greater than the aperture of the excitation beam path.

FIG. 6 shows possible forms of blocking out (18).

FIG. 6a shows the shape of the blocking out when the image of the excitation spot in the image plane (8) does not move. This is the case when the specimen is not to be scanned or when the excitation light and the useful light are deflected by the scanning mirror (FIGS. 9, 14). In this case, only the center part of the pupil is blocked out. In this case, the confocal diaphragm (8a) is a pinhole.

Like FIG. 5, FIG. 6b shows the shape of the blocking out when only the excitation light is deflected by a scanning mirror (14) that is only tilted about one axis. The blocked out strip (18) must lie parallel to the line on which the excitation spot moves back and forth in the object plane. The confocal diaphragm (8a) is then constructed as a slit diaphragm whose slit also lies parallel to the movement direction of the excitation spot in the object plane.

While the foregoing description and drawings represent the present invention, it will be obvious to those skilled in the art that various changes may be made therein without departing from the true spirit and scope of the present invention.

What is claimed is:

1. A scanning arrangement for detecting fluorescent light of an illuminated specimen, comprising:

at least one scanning mirror, an objective and a mirror arranged in the pupil plane of the objective for directing excitation light to the specimen;

said pupil plane mirror being at least partially part of a diaphragm, fluorescent light from the specimen passing essentially past the diaphragm in the direction of a detector via a slit or a pinhole.

2. The arrangement according to claim 1, including a strip-shaped diaphragm in the detection beam path.

3. The arrangement according to claim 2, wherein a slit diaphragm is arranged in an intermediate image plane of projection optics and the slit lies parallel to the strip-shaped diaphragm.

4. The arrangement according to claim 1, wherein the fluorescent light is imaged via projection optics in the direction of the detector.

5. A scanning arrangement for detecting fluorescent light of an illuminated specimen, comprising:

a scanning mirror;

an objective; and a pupil plane mirror arranged in the pupil plane of the objective for directing excitation light coming from the scanning mirror to the specimen;

the pupil plane mirror being at least part of a pupil diaphragm, fluorescent light from the specimen passing past the pupil diaphragm in the direction of a detector via a slit or a pinhole.

6. The scanning arrangement according to claim 5, further comprising a strip-shaped diaphragm positioned in the detection beam path.

7. The scanning arrangement according to claim 6, wherein a strip-shaped diaphragm positioned in an intermediate image plane of the projection optics and the slit or pinhole lies parallel to the strip-shaped diaphragm.

8. The scanning arrangement according to claim 5, further comprising projection optics arranged in the direction of the detector and through which the fluorescent light is imaged.

* * * * *